US012629178B2

(12) United States Patent
Melton et al.

(10) Patent No.: US 12,629,178 B2
(45) Date of Patent: May 19, 2026

(54) SURGICAL IMPLANT AND METHODS OF ADDITIVE MANUFACTURING

(71) Applicant: Stryker Corporation, Portage, MI (US)

(72) Inventors: Patrick Melton, Seattle, WA (US); Michael Prosser, Mount Pleasant, SC (US)

(73) Assignee: Stryker Corporation, Portage, MI (US)

( * ) Notice: Subject to any disclaimer, the term of this patent is extended or adjusted under 35 U.S.C. 154(b) by 372 days.

(21) Appl. No.: 18/203,128

(22) Filed: May 30, 2023

(65) Prior Publication Data

US 2023/0293208 A1     Sep. 21, 2023

Related U.S. Application Data

(63) Continuation of application No. 17/226,453, filed on Apr. 9, 2021, now Pat. No. 11,701,146, which is a
(Continued)

(51) Int. Cl.
*A61B 17/70*        (2006.01)
*A61B 17/80*        (2006.01)
(Continued)

(52) U.S. Cl.
CPC ...... *A61B 17/7035* (2013.01); *A61B 17/7032* (2013.01); *A61B 17/7037* (2013.01);
(Continued)

(58) Field of Classification Search
CPC ............ A61B 17/7032; A61B 17/7034; A61B 17/7035; A61B 17/7049; A61B 17/86;
(Continued)

(56) References Cited

U.S. PATENT DOCUMENTS

| | | |
|---|---|---|
| 4,798,610 A | 1/1989 | Averill et al. |
| 5,286,573 A | 2/1994 | Prinz et al. |

(Continued)

FOREIGN PATENT DOCUMENTS

| | | |
|---|---|---|
| DE | 102008024281 A1 | 12/2009 |
| DE | 102008024288 A1 | 12/2009 |

(Continued)

OTHER PUBLICATIONS

International Search Report and Written Opinion issued in corresponding PCT Appln. No. PCT/US2018/041238.
(Continued)

*Primary Examiner* — Jacqueline T Johanas
*Assistant Examiner* — Christina Negrellirodriguez
(74) *Attorney, Agent, or Firm* — Lerner David LLP

(57)        ABSTRACT

A method of manufacturing a surgical implant includes simultaneously forming a first component and a second component of the surgical implant. Formation of the first and second components includes depositing a first quantity of material to a building platform and fusing the first quantity of material to form a first layer of the first and second components. The method of manufacturing also includes depositing a second quantity of material over the first layer of the first and second components and fusing the second quantity of material to form a second layer of the first and second components. The surgical implant is fully assembled upon the completion of the formation of the first and second components.

19 Claims, 12 Drawing Sheets

Related U.S. Application Data continuation of application No. 15/643,603, filed on Jul. 7, 2017, now Pat. No. 11,006,981.

(51) Int. Cl.

| | |
|---|---|
| *A61B 17/86* | (2006.01) |
| *A61B 34/10* | (2016.01) |
| *A61F 2/30* | (2006.01) |
| *A61F 2/44* | (2006.01) |
| *B22F 7/06* | (2006.01) |
| *B22F 10/00* | (2021.01) |
| *B29C 64/153* | (2017.01) |
| *B29C 64/393* | (2017.01) |
| *B33Y 50/02* | (2015.01) |
| *B33Y 70/00* | (2020.01) |
| *A61B 17/00* | (2006.01) |
| *B22F 10/14* | (2021.01) |
| *B22F 10/25* | (2021.01) |
| *B22F 10/28* | (2021.01) |
| *B22F 10/40* | (2021.01) |
| *B22F 10/60* | (2021.01) |
| *B22F 10/64* | (2021.01) |
| *B22F 10/66* | (2021.01) |
| *B22F 10/68* | (2021.01) |
| *B22F 10/80* | (2021.01) |
| *B22F 12/00* | (2021.01) |
| *B29L 31/00* | (2006.01) |
| *B33Y 10/00* | (2015.01) |
| *B33Y 80/00* | (2015.01) |

(52) U.S. Cl.

CPC .......... *A61B 17/7049* (2013.01); *A61B 17/80* (2013.01); *A61B 17/86* (2013.01); *A61B 34/10* (2016.02); *A61F 2/30942* (2013.01); *A61F 2/442* (2013.01); *A61F 2/4455* (2013.01); *B22F 7/06* (2013.01); *B22F 10/00* (2021.01); *B29C 64/153* (2017.08); *B29C 64/393* (2017.08); *B33Y 50/02* (2014.12); *B33Y 70/00* (2014.12); *A61B 2017/00526* (2013.01); *A61B 2034/108* (2016.02); *A61F 2002/30578* (2013.01); *A61F 2002/30787* (2013.01); *A61F 2002/3085* (2013.01); *A61F 2002/30952* (2013.01); *A61F 2002/30971* (2013.01); *A61F 2002/30985* (2013.01); *B22F 10/14* (2021.01); *B22F 10/25* (2021.01); *B22F 10/28* (2021.01); *B22F 10/40* (2021.01); *B22F 10/60* (2021.01); *B22F 10/64* (2021.01); *B22F 10/66* (2021.01); *B22F 10/68* (2021.01); *B22F 10/80* (2021.01); *B22F 12/38* (2021.01); *B29L 2031/753* (2013.01); *B33Y 10/00* (2014.12); *B33Y 80/00* (2014.12)

(58) Field of Classification Search

CPC ..... B29C 64/153; B29C 64/393; B22F 10/00; B33Y 80/10

USPC .......................................... 606/246, 300–321

See application file for complete search history.

(56) References Cited

U.S. PATENT DOCUMENTS

| | | | |
|---|---|---|---|
| 5,411,523 | A | 5/1995 | Goble |
| 5,466,237 | A | 11/1995 | Byrd, III et al. |
| 5,474,555 | A | 12/1995 | Puno et al. |
| 5,534,031 | A | 7/1996 | Matsuzaki et al. |
| 5,595,703 | A | 1/1997 | Swaelens et al. |
| 5,733,286 | A | 3/1998 | Errico et al. |
| 5,768,134 | A | 6/1998 | Swaelens et al. |
| 5,943,235 | A | 8/1999 | Earl et al. |
| 5,968,098 | A | 10/1999 | Winslow |
| 6,010,502 | A | 1/2000 | Bagby |
| 6,039,762 | A | 3/2000 | McKay |
| 6,391,058 | B1 | 5/2002 | Kuslich et al. |
| 6,432,107 | B1 | 8/2002 | Ferree |
| 6,520,996 | B1 | 2/2003 | Manasas et al. |
| 6,530,955 | B2 | 3/2003 | Boyle et al. |
| 6,530,956 | B1 | 3/2003 | Mansmann |
| 6,645,227 | B2 | 11/2003 | Fallin et al. |
| 6,716,247 | B2 | 4/2004 | Michelson |
| 6,736,820 | B2 | 5/2004 | Biedermann et al. |
| 6,758,849 | B1 | 7/2004 | Michelson |
| 7,087,057 | B2 | 8/2006 | Konieczynski et al. |
| 7,238,206 | B2 | 7/2007 | Lange et al. |
| 7,509,183 | B2 | 3/2009 | Lin et al. |
| 7,537,664 | B2 | 5/2009 | O'Neill et al. |
| 7,665,979 | B2 | 2/2010 | Heugel |
| 7,909,872 | B2 | 3/2011 | Zipnick et al. |
| 8,275,594 | B2 | 9/2012 | Lin et al. |
| 8,287,576 | B2 | 10/2012 | Barrus |
| 8,349,015 | B2 | 1/2013 | Bae et al. |
| 8,403,986 | B2 | 3/2013 | Michelson |
| 8,439,977 | B2 | 5/2013 | Kostuik et al. |
| 8,449,585 | B2 | 5/2013 | Wallenstein et al. |
| 8,584,853 | B2 | 11/2013 | Knight et al. |
| 8,585,761 | B2 | 11/2013 | Theofilos |
| 8,590,157 | B2 | 11/2013 | Kruth et al. |
| 8,636,738 | B2 | 1/2014 | McClintock et al. |
| 8,673,011 | B2 | 3/2014 | Theofilos et al. |
| 8,697,231 | B2 | 4/2014 | Longepied et al. |
| 8,728,387 | B2 | 5/2014 | Jones et al. |
| 8,734,491 | B2 | 5/2014 | Seavey |
| 8,784,721 | B2 | 7/2014 | Philippi et al. |
| 8,801,791 | B2 | 8/2014 | Soo et al. |
| 8,814,919 | B2 | 8/2014 | Barrus et al. |
| 8,843,229 | B2 | 9/2014 | Vanasse et al. |
| 8,870,930 | B2 | 10/2014 | Carbone et al. |
| 8,870,957 | B2 | 10/2014 | Vraney et al. |
| 8,882,840 | B2 | 11/2014 | Mcclintock et al. |
| 8,894,694 | B2 | 11/2014 | Brandon |
| 8,903,533 | B2 | 12/2014 | Eggers et al. |
| 8,932,356 | B2 | 1/2015 | Kraus |
| 8,967,990 | B2 | 3/2015 | Weidinger et al. |
| 8,999,711 | B2 | 4/2015 | Harlow et al. |
| 9,011,982 | B2 | 4/2015 | Muller et al. |
| 9,135,374 | B2 | 9/2015 | Jones et al. |
| 9,180,010 | B2 | 11/2015 | Dong et al. |
| 9,283,078 | B2 | 3/2016 | Roels et al. |
| 9,393,049 | B2 | 7/2016 | Jones et al. |
| 9,456,901 | B2 | 10/2016 | Jones et al. |
| 9,480,577 | B2 | 11/2016 | Despiau et al. |
| 9,566,163 | B2 | 2/2017 | Suddaby et al. |
| 9,572,680 | B2 | 2/2017 | Theofilos et al. |
| 10,850,193 | B2 | 12/2020 | DeRidder et al. |
| 11,298,747 | B2 | 4/2022 | Klein et al. |
| 2001/0047207 | A1 | 11/2001 | Michelson |
| 2001/0047208 | A1 | 11/2001 | Michelson |
| 2002/0128714 | A1 | 9/2002 | Manasas et al. |
| 2003/0040798 | A1 | 2/2003 | Michelson |
| 2003/0135276 | A1 | 7/2003 | Eckman |
| 2004/0024400 | A1 | 2/2004 | Michelson |
| 2004/0243237 | A1 | 12/2004 | Unwin et al. |
| 2004/0249471 | A1 | 12/2004 | Bindseil et al. |
| 2005/0021151 | A1 | 1/2005 | Landis |
| 2005/0149192 | A1 | 7/2005 | Zucherman et al. |
| 2005/0177238 | A1 | 8/2005 | Khandkar et al. |
| 2006/0058888 | A1 | 3/2006 | Hunter et al. |
| 2007/0116734 | A1 | 5/2007 | Akash |
| 2007/0233272 | A1 | 10/2007 | Boyce et al. |
| 2009/0093881 | A1 | 4/2009 | Bandyopadhyay et al. |
| 2009/0270922 | A1 | 10/2009 | Biedermann et al. |
| 2009/0291308 | A1 | 11/2009 | Pfister et al. |
| 2010/0100131 | A1 | 4/2010 | Wallenstein |
| 2010/0137990 | A1 | 6/2010 | Apatsidis et al. |
| 2010/0228369 | A1 | 9/2010 | Eggers et al. |
| 2010/0249926 | A1* | 9/2010 | Kirschman .......... A61B 17/866 606/301 |

(56) References Cited

U.S. PATENT DOCUMENTS

| | | |
|---|---|---|
| 2010/0312282 A1 | 12/2010 | Abdou |
| 2011/0144752 A1 | 6/2011 | Defelice et al. |
| 2011/0165340 A1 | 7/2011 | Baumann |
| 2011/0168091 A1 | 7/2011 | Baumann et al. |
| 2011/0190904 A1 | 8/2011 | Lechmann et al. |
| 2011/0301709 A1 | 12/2011 | Kraus et al. |
| 2012/0046750 A1 | 2/2012 | Obrigkeit et al. |
| 2012/0143334 A1 | 6/2012 | Boyce et al. |
| 2012/0158062 A1 | 6/2012 | Nunley et al. |
| 2012/0179261 A1 | 7/2012 | Soo |
| 2012/0191188 A1 | 7/2012 | Huang |
| 2012/0191189 A1 | 7/2012 | Huang |
| 2012/0310364 A1 | 12/2012 | Li et al. |
| 2013/0046345 A1 | 2/2013 | Jones et al. |
| 2013/0046348 A1 | 2/2013 | Black |
| 2013/0110243 A1 | 5/2013 | Patterson et al. |
| 2013/0116793 A1 | 5/2013 | Kloss |
| 2013/0171019 A1 | 7/2013 | Gessler et al. |
| 2013/0197645 A1 | 8/2013 | Assell et al. |
| 2013/0245697 A1 | 9/2013 | Hulliger |
| 2013/0273131 A1 | 10/2013 | Frangov et al. |
| 2013/0345758 A1* | 12/2013 | Biedermann ...... A61B 17/7037 606/279 |
| 2014/0086780 A1 | 3/2014 | Miller et al. |
| 2014/0088716 A1 | 3/2014 | Zubok et al. |
| 2014/0107785 A1 | 4/2014 | Geisler et al. |
| 2014/0107786 A1 | 4/2014 | Geisler et al. |
| 2014/0172111 A1 | 6/2014 | Lang et al. |
| 2014/0277503 A1 | 9/2014 | Mendel et al. |
| 2015/0018956 A1 | 1/2015 | Steinmann et al. |
| 2015/0045924 A1 | 2/2015 | Cluckers et al. |
| 2015/0134063 A1 | 5/2015 | Steinmann et al. |
| 2015/0142158 A1 | 5/2015 | Szwedka |
| 2015/0272628 A1 | 10/2015 | Kishan et al. |
| 2015/0352784 A1 | 12/2015 | Lechmann et al. |
| 2015/0367575 A1 | 12/2015 | Roels et al. |
| 2016/0058575 A1 | 3/2016 | Sutterlin et al. |
| 2016/0157908 A1* | 6/2016 | Cawley ................. A61F 2/3094 606/301 |
| 2016/0166396 A1 | 6/2016 | McClintock |
| 2017/0079807 A1 | 3/2017 | Wallenstein et al. |
| 2019/0038318 A1 | 2/2019 | Tempco et al. |
| 2019/0314160 A1 | 10/2019 | Wang et al. |
| 2021/0379884 A1 | 12/2021 | O'Neill et al. |

FOREIGN PATENT DOCUMENTS

| | | |
|---|---|---|
| EP | 0425542 B1 | 3/1995 |
| EP | 1464307 A1 | 10/2004 |
| EP | 1905391 B1 | 1/2010 |
| EP | 2145913 A1 | 1/2010 |
| EP | 2457538 A1 | 5/2012 |
| EP | 1772108 B1 | 11/2015 |
| EP | 3415108 A1 | 12/2018 |
| EP | 3474783 A2 | 5/2019 |
| JP | 2008513120 A | 5/2008 |
| JP | 2009516544 A | 4/2009 |
| JP | 2009261947 A | 11/2009 |
| JP | 2013516235 A | 5/2013 |
| JP | 2015208669 A | 11/2015 |
| JP | 2015532858 A | 11/2015 |
| JP | 2015213530 A | 12/2015 |
| WO | 9000037 A1 | 1/1990 |
| WO | 9405235 A1 | 3/1994 |
| WO | 9419174 A1 | 9/1994 |
| WO | 9510248 A1 | 4/1995 |
| WO | 9532673 A1 | 12/1995 |
| WO | 9608360 A1 | 3/1996 |
| WO | 9628117 A1 | 9/1996 |
| WO | 9640015 A1 | 12/1996 |
| WO | 9640019 A1 | 12/1996 |
| WO | 9734546 A1 | 9/1997 |
| WO | 0025707 A1 | 5/2000 |
| WO | 0040177 A1 | 7/2000 |
| WO | 0066045 A1 | 11/2000 |
| WO | 0202151 A2 | 1/2002 |
| WO | 0230337 A2 | 4/2002 |
| WO | 02080820 A1 | 10/2002 |
| WO | 2006101837 A2 | 9/2006 |
| WO | 2009068021 A1 | 6/2009 |
| WO | 2011006155 A1 | 1/2011 |
| WO | 2011030017 A1 | 3/2011 |
| WO | 2011156504 A2 | 12/2011 |
| WO | 201317647 A1 | 2/2013 |
| WO | 2013155500 A1 | 10/2013 |
| WO | 2013156545 A1 | 10/2013 |
| WO | 201496294 A1 | 6/2014 |
| WO | 2014145527 A2 | 9/2014 |
| WO | 2016112175 A1 | 7/2016 |
| WO | 2017027873 A1 | 2/2017 |
| WO | 2018002711 A2 | 1/2018 |

OTHER PUBLICATIONS

Extended European Search Report for EP 16 15 2952 dated Jul. 1, 2016.

Fukuda A, Takemoto M, Tanaka K, Fujibayashi S, Pattanayak DK, Matsushita T, Sasaki K, Nishida N, Kokubo T, Nakamura T. Bone ingrowth into pores of lotus stem-type bioactive titanium implants fabricated using rapid prototyping technique. Bioceramics Development and Applications. Jan. 1, 2011;1, 3 pages.

Williams et al., CT Evaluation of Lumbar Interbody Fusion: Current Concepts, AJNR Am J Neuroradiol 26:2057-2066, Sep. 2005.

Cunningham et al, Design of Interbody Fusion Cages: Historical Considerations and Current Perspectives in Cage Technology; Surgical Techniques, Spinal Implants, pp. 421-465, 2006.

Akamaru et al., Healing of Autologous Bone in a Titanium Mesh Cage Used in Anterior Column Reconstruction After Total Spondylectomy; SPINE vol. 27, No. 13, pp. E329-E333, 2002.

Lin et al., Interbody Fusion Cage Design Using Integrated Global Layout and Local Microstructure Topology Optimization; SPINE, vol. 29, No. 16, pp. 1747-1754, 2004.

McAfee, Interbody Fusion Cages in Reconstructive Operations on the Spine, The Journal of Bone and Joint Surgery Incorporated, vol. 81A, No. 6, Jun. 1999, pp. 859-880.

Zdeblick, et al., LT-CAGE Lumbar Tapered Fusion Device Surgical Technique, Medtronic, pp. 1-25, 2000.

Kuslich, Lumbar Interbody Cage Fusion for Back Pain: An Update on the Bak (Bagby and Kuslich) System, SPINE: State of the Art Reviews; vol. 13, No. 2, May 1999, pp. 295-311.

Cheung et al., Spinal Instrumentation Overview in Lumbar Degenerative Disorders: Cages, Lumbar Spine: Official Publication of the International Society for the Study of Lumbar Spine (3), pp. 286-291, 2004.

Sasso, Screws, Cages or Both?, <http://www.spineuniverse.com/professional/technology/surgical/thoracic/>, pp. 1-11, Sep. 2012.

Costa et al., Stand-alone cage for posterior lumbar interbody fusion in the treatment of high-degree degenerative disc disease: design of a new device for an "old" technique. A prospective study on a series of 116 patients, Eur Spine J, May 2011: 20 (Suppl 1), pp. 46-56.

Lin, et al. Structural and mechanical evaluations of a topology optimized titanium interbody fusion cage fabricated by selective laser melting process, Journal of Biomedical Materials Research Part A DOI 10.1 002/jbm.a, pp. 272-279, Apr. 2007.

Chong et al., The design evolution of interbody cages in anterior cervical discectomy and fusion: a systematic review; BMC Musculoskeletal Disorders Apr. 2015 16:99, pp. 1-20.

Bridwell et al.., Specialty Update, What's New in Spine Surgery, The Journal of Bone and Joint Surgery, Incorporated, pp. 1022-1030, Core 1st page of article, Jun. 2015.

EBI Spine, Promotional flyer, 1 page 2005.

Synthes Contact Fusion Cage, Technique Guide, 2007, pp. 1-16.

Stryker, Tlritanium basic science summary, technical monograph, pp. 1-2, 2016.

Sofamar Danek Interfix Thread Fusion Device, pp. 32-45, 1999.

Kim et al. Spinal Instrumentation Surgical Techniques, Thieme Medical publishers, 2004, pp. 232-245, 518-524, p. 32-537, 736-743, 795-800.

(56) References Cited

OTHER PUBLICATIONS

Schultz, Christian K., et al., U.S. Appl. No. 62/478,162, filed Mar. 29, 2017, titled "Spinal Implant System".

Willis, Steven, et al., U.S. Appl. No. 14/994,749, filed Jan. 13, 2016, titled "Spinal Implant With Porous And Solid Surfaces".

ACP 1 Anterior Cervical Plating System, Surgical Technique, Stryker Spine, 2016.

Extended European Search Report and Written Opinion for EP Application No. 18173999.6, mailed Nov. 19, 2018.

Extended European Search Report for Application No. EP18827686. 9, dated Jun. 29, 2020, pp. 1-3.

* cited by examiner

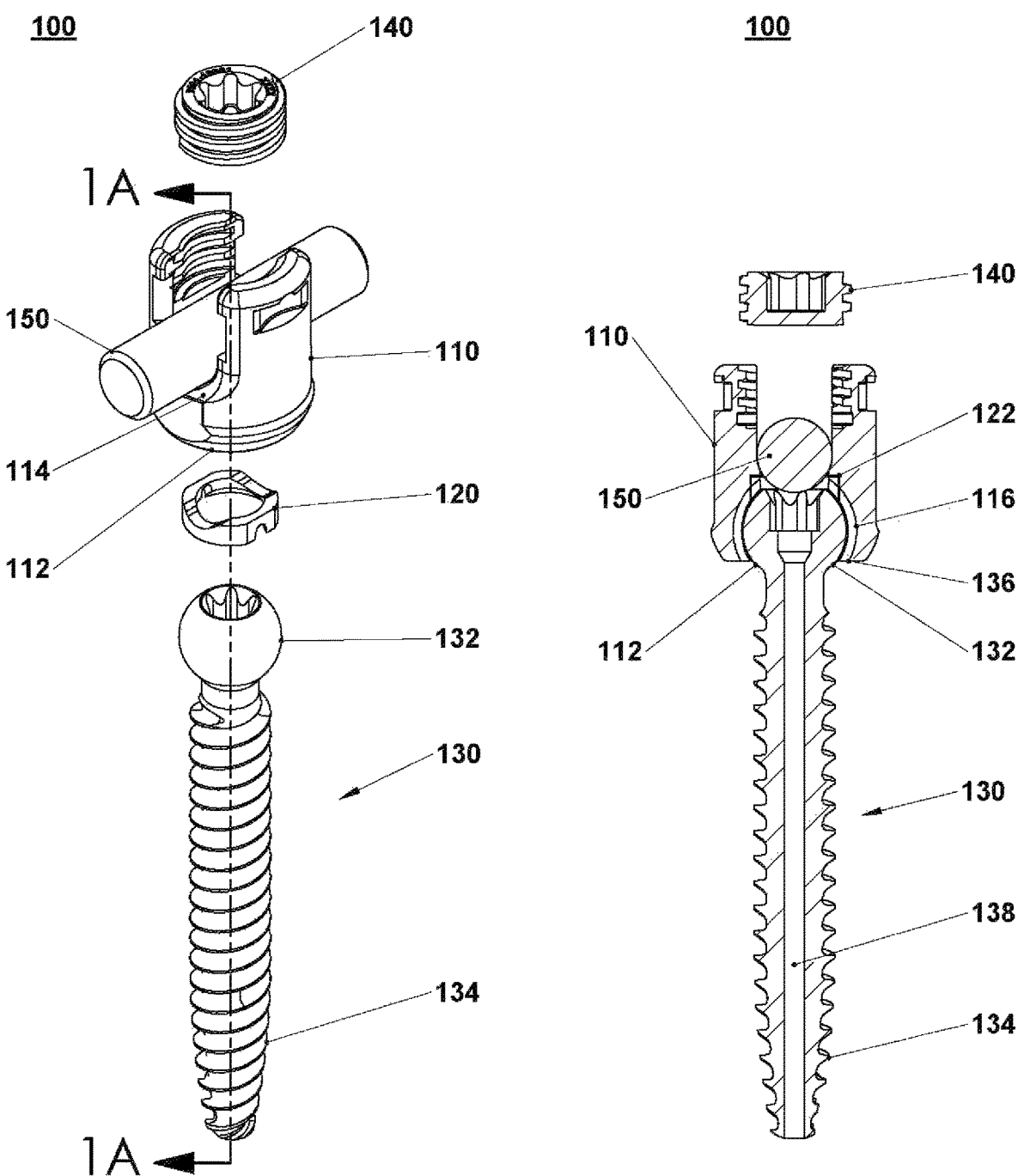
FIG. 1                    FIG. 1A

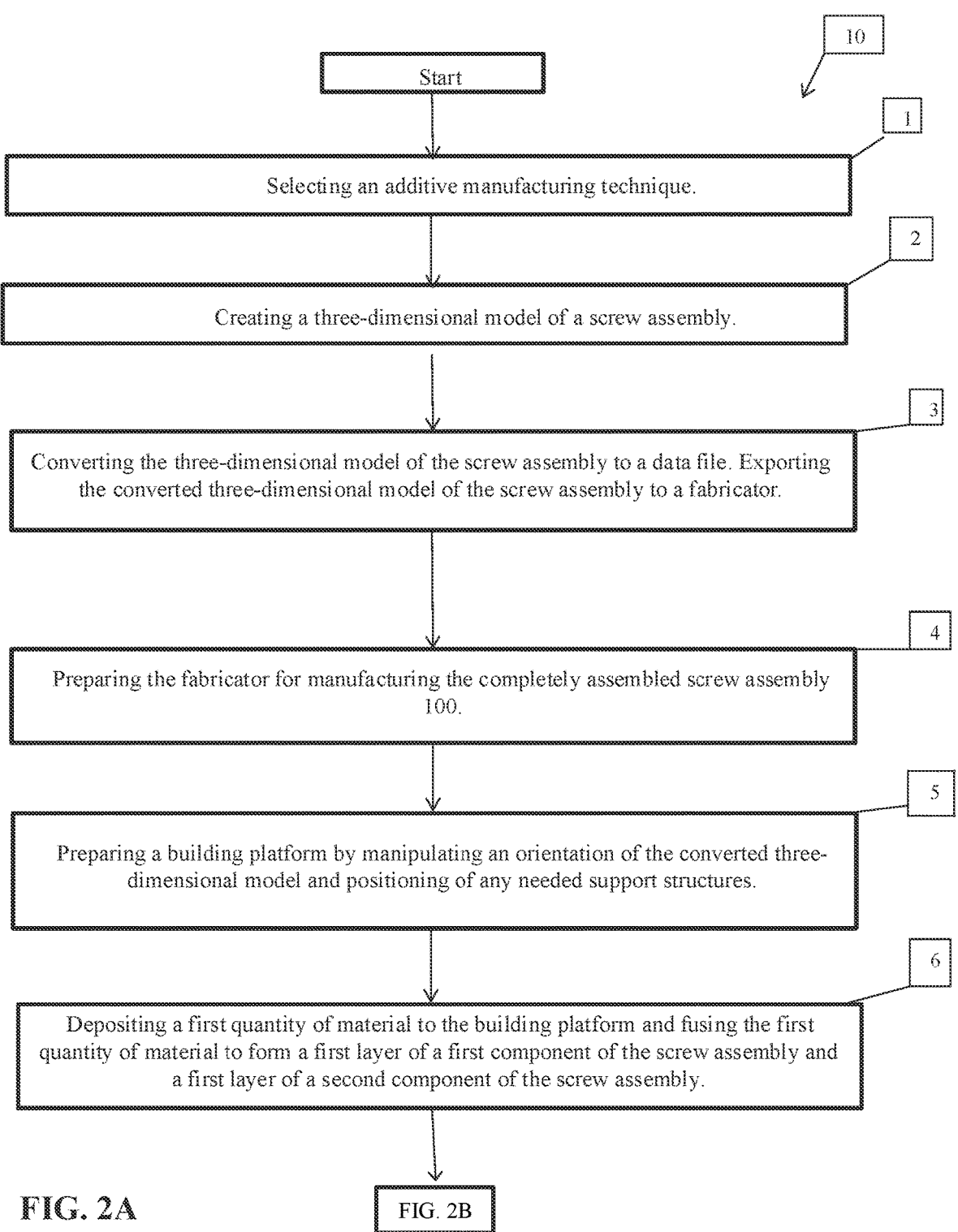

10

Start

1

Selecting an additive manufacturing technique.

2

Creating a three-dimensional model of a screw assembly.

3

Converting the three-dimensional model of the screw assembly to a data file. Exporting the converted three-dimensional model of the screw assembly to a fabricator.

4

Preparing the fabricator for manufacturing the completely assembled screw assembly 100.

5

Preparing a building platform by manipulating an orientation of the converted three-dimensional model and positioning of any needed support structures.

6

Depositing a first quantity of material to the building platform and fusing the first quantity of material to form a first layer of a first component of the screw assembly and a first layer of a second component of the screw assembly.

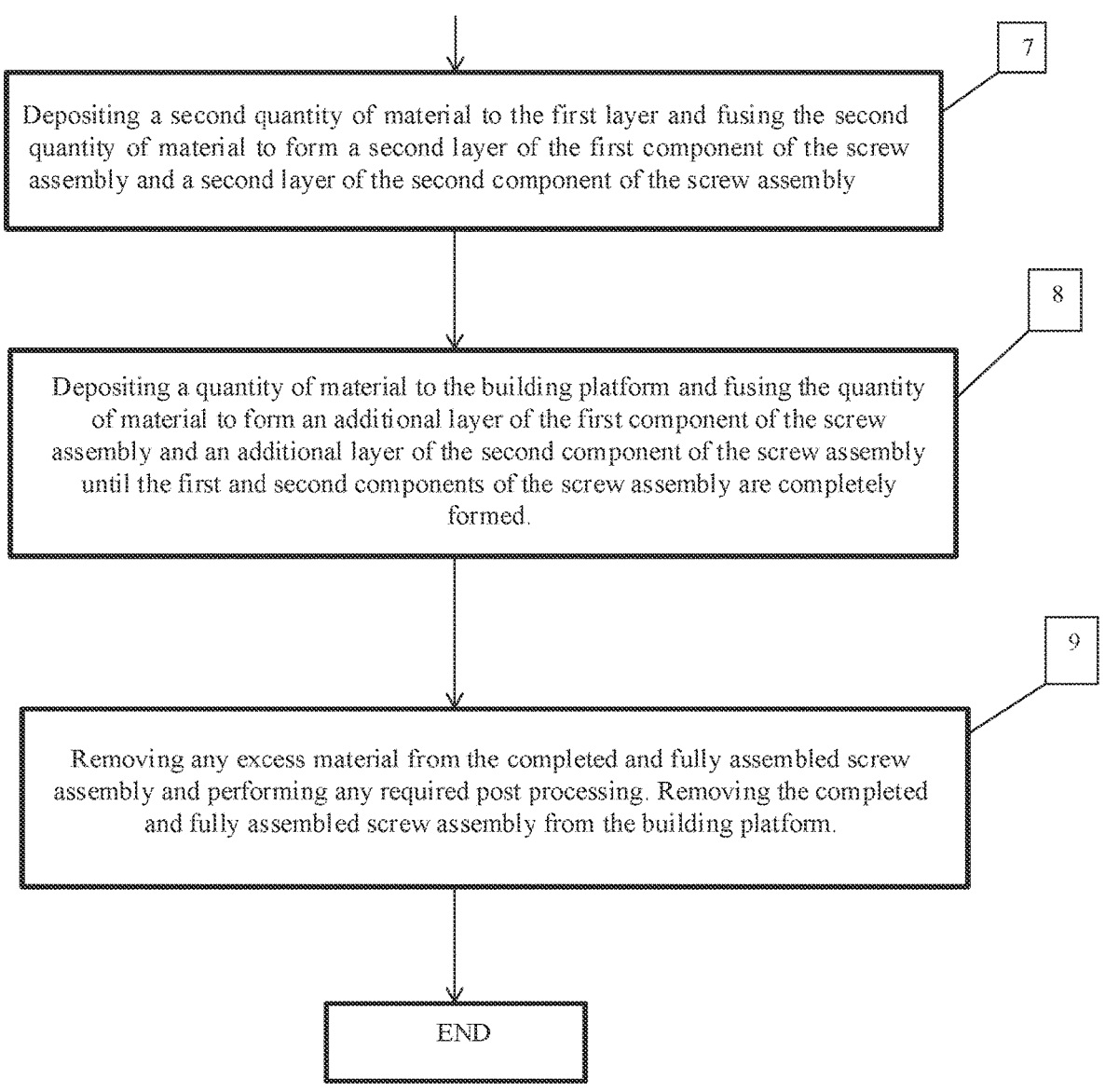

7

Depositing a second quantity of material to the first layer and fusing the second quantity of material to form a second layer of the first component of the screw assembly and a second layer of the second component of the screw assembly

8

Depositing a quantity of material to the building platform and fusing the quantity of material to form an additional layer of the first component of the screw assembly and an additional layer of the second component of the screw assembly until the first and second components of the screw assembly are completely formed.

9

Removing any excess material from the completed and fully assembled screw assembly and performing any required post processing. Removing the completed and fully assembled screw assembly from the building platform.

END

FIG. 2B

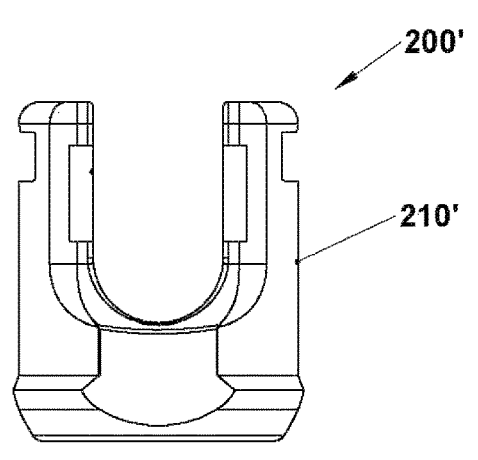
200'
210'
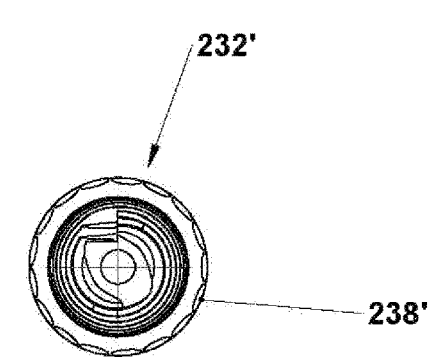
232'
238'
FIG. 5A
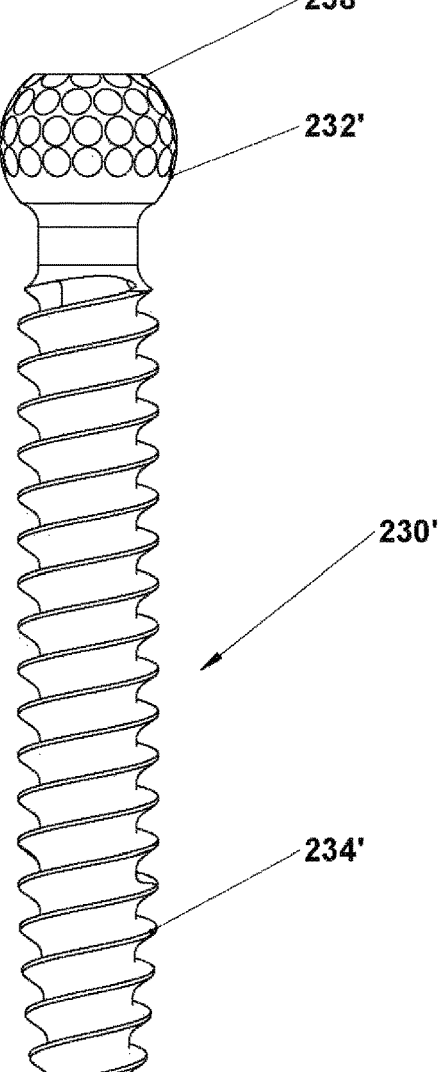
238'
232'
230'
234'
FIG. 5
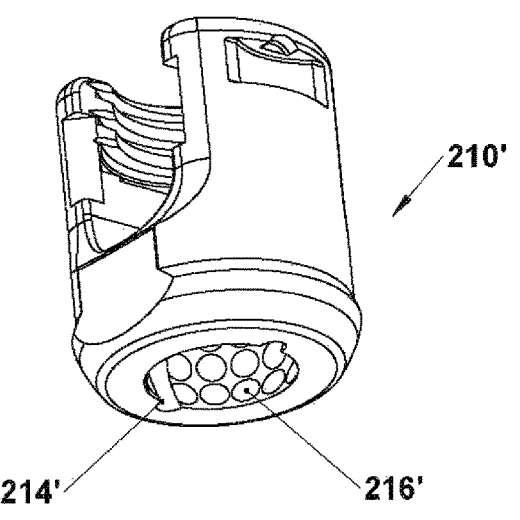
210'
214'
216'
FIG. 5B

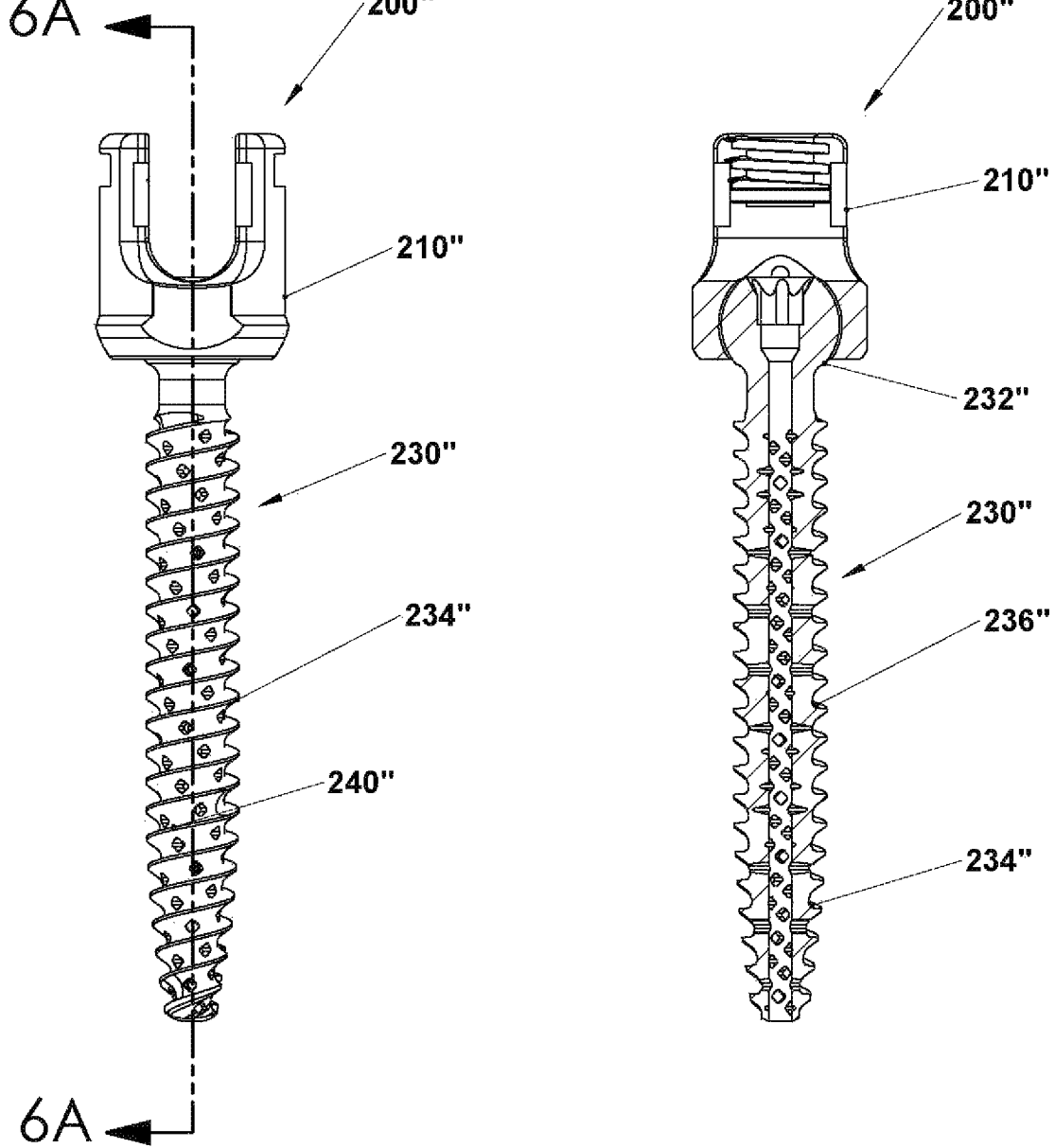
FIG. 6                FIG. 6A

500

SURGICAL IMPLANT AND METHODS OF ADDITIVE MANUFACTURING

CROSS-REFERENCE TO RELATED APPLICATIONS

The present application is a continuation of U.S. patent application Ser. No. 17/226,453, filed Apr. 9, 2021, which is a continuation of U.S. patent application Ser. No. 15/643,603, filed Jul. 7, 2017, now U.S. Pat. No. 11,006,981, the entire disclosures of which are hereby incorporated by reference herein.

TECHNICAL FIELD

This disclosure relates generally to a surgical implant. More specifically, the present disclosure relates to a surgical implant including multiple components and a method of manufacturing an assembled surgical implant.

BACKGROUND

Spinal fixation apparatuses are widely employed in surgical procedure for correcting spinal injuries and diseases. When the disc has degenerated to the point of requiring removal, there are a variety of interbody implants that are utilized to take the place of the disc. These include polyetheretherketone ("PEEK") interbody spacers, metal cages, cadaver, and human bone implants. In order to facilitate stabilizing the spine and keeping the interbody in position, other implants are commonly employed, including longitudinally linked rods secured to coupling elements, which in turn are secured to the bone by spinal bone fixation fasteners such as pedicle screws, hooks, and others. An opposing pair of longitudinally linked rods is commonly disposed along the long axis of the spine via a posterior approach. Pedicle screws can be manufactured from any biocompatible material, including cobalt chrome, stainless steel, titanium, and PEEK.

Typically, pedicle screws are formed using traditional methods of manufacturing, such as welding, fastening, machining, and/or molding. Also, usually one or more components of the pedicle screw are manually assembled. These methods of manufacturing and assembly use material inefficiently and require manufacturing and assembly to occur separately, which requires additional time prior to shipment. Further, traditional methods of manufacturing limit the design options of pedicle screws.

Therefore, a need exists for a cost and time effective method of manufacturing for a pedicle screw and/or other orthopedic, spinal implants, or fixation apparatuses.

SUMMARY

A method of manufacturing a surgical implant includes simultaneously forming a first component and a second component of the surgical implant. Formation of the first and second components includes depositing a first quantity of material to a building platform and fusing the first quantity of material to form a first layer of the first and second components. The method of manufacturing also includes depositing a second quantity of material over the first layer of the first and second components and fusing the second quantity of material to form a second layer of the first and second components. The surgical implant is fully assembled upon the completion of the formation of the first and second components, without the need for mechanical assembly of the parts.

In one embodiment, the method further includes providing a description of the surgical implant to be manufactured, the description of the surgical device includes the first component and the second component, wherein the first and second components when formed are movable in relation to one another. The description of the surgical implant is provided in the form of a computer-aided design or manufacturing (CAD/CAM) file. The method also includes selecting the material for the first component and the material for the second component from a group consisting of stainless steel, titanium, cobalt chrome, titanium alloy, polyethylene, polycarbonate, PEEK, polypropylene, and polysulfone. The fully assembled surgical implant is removed from the building platform. Also, any additional material is removed from the fully assembled surgical implant. Subsequent finishing steps such as washing or polishing are contemplated. The first and second components are each monolithically formed via the method of manufacturing.

In one embodiment, the first component includes a bone screw having a bone screw head and a threaded shaft and the second component includes a rod-receiving housing the bone screw head captured within the housing.

In another embodiment, the method further includes forming a third component of the surgical implant simultaneously with forming the first and second components of the surgical implant.

An orthopedic implant includes a monolithic first component and a monolithic second component. The monolithic first component has a hollow interior portion and at least one opening. The monolithic second component has a head portion disposed within the hollow interior portion and a shaft portion extending through the at least one opening of the monolithic first component. The head portion is configured and dimensioned to be larger than the at least one opening and therefore unable to pass therethrough.

The monolithic first component includes a spinal rod connector member. The monolithic second component includes a receiving arm. The spinal rod connector member and the receiving arm define a ball joint assembly.

In another embodiment, the monolithic first component includes a housing. The monolithic second component includes a bone screw member including a head and a shaft. The head is disposed within the housing and the shaft extends from the housing through the at least one opening of the first monolithic component. The housing also includes a U-shaped end configured to receive a rod. The orthopedic implant is fully assembled when the monolithic second component is positioned within the first component. The monolithic first component and the monolithic second component are movable relative to one another. The monolithic first component and the monolithic second component are movable relative to one another in one of a polyaxial, rotatable, monoaxial, or uniaxial motion.

Another method of fabricating a surgical implant includes a depositing a first layer of material on a building platform; fusing the first layer of material to form a first thickness of the surgical implant; depositing a plurality of additional layers of material onto the first thickness of the surgical implant; and fusing the plurality of additional layers of material to the first thickness of the surgical implant to form a second thickness of the surgical implant. The surgical implant includes a housing having a U-shaped channel for receiving a spinal rod and a screw with a head polyaxially disposed in the housing and a threaded shaft extending from the head.

In one embodiment, the method further includes providing a description of the surgical implant to be fabricated. The description of the surgical device includes the housing and the screw. The housing and the screw are movable in relation to one another. The description of the surgical implant is provided in the form of a computer-aided design or manufacturing (CAD/CAM) file. The computer-aided design or manufacturing (CAD/CAM) file is converted to a STL file. The fully assembled surgical implant is removed from the building platform.

A surgical implant includes a screw assembly and a bone plate. The screw assembly includes a head and a threaded shaft. The threaded shaft extends from the head and is removable coupled thereto. The bone plate defines at least one aperture configured to receive the head of the screw assembly. Each of a proximal opening and a distal opening of the at least one aperture defines a smaller circumference than a circumference of the head.

The screw assembly and the bone plate are manufactured simultaneously using a layer-by-layer technique. The head of the screw assembly is formed within the at least one aperture of the bone plate.

A method of implanting a surgical implant includes selecting a length of a threaded shaft of a screw assembly; inserting the threaded shaft of the screw assembly within a patient; connecting a head of the screw assembly and a bone plate; and tightening the head of the screw assembly thereby securing the bone plate and the screw assembly to the patient. The head of the screw assembly is housed within the bone.

BRIEF DESCRIPTION OF THE DRAWINGS

Various embodiments of the present disclosure are described herein below with reference to the drawings, wherein:

FIG. 1 is an isometric view, with parts separated, of a three piece surgical implant according to an embodiment of the present disclosure;

FIG. 1A is a cross-section of the three piece surgical implant of FIG. 1 as taken along section line 1A-1A shown in FIG. 1;

FIGS. 2A and 2B are a flow chart illustrating a method of additive manufacturing according to the present disclosure;

FIG. 5 is an isometric view, with parts separated, of a two piece surgical implant according to another embodiment of the present disclosure;

FIG. 5A is a top view of a bone screw member of the two piece surgical implant of FIG. 5;

FIG. 5B is a perspective view of a housing of the surgical implant of FIG. 5;

FIG. 6 is an isometric view of a surgical implant according to a further embodiment of the present disclosure;

FIG. 6A is a cross-section of a surgical implant of FIG. 6 as taken along section 6A-6A shown in FIG. 6;

DETAILED DESCRIPTION

Figure 3:
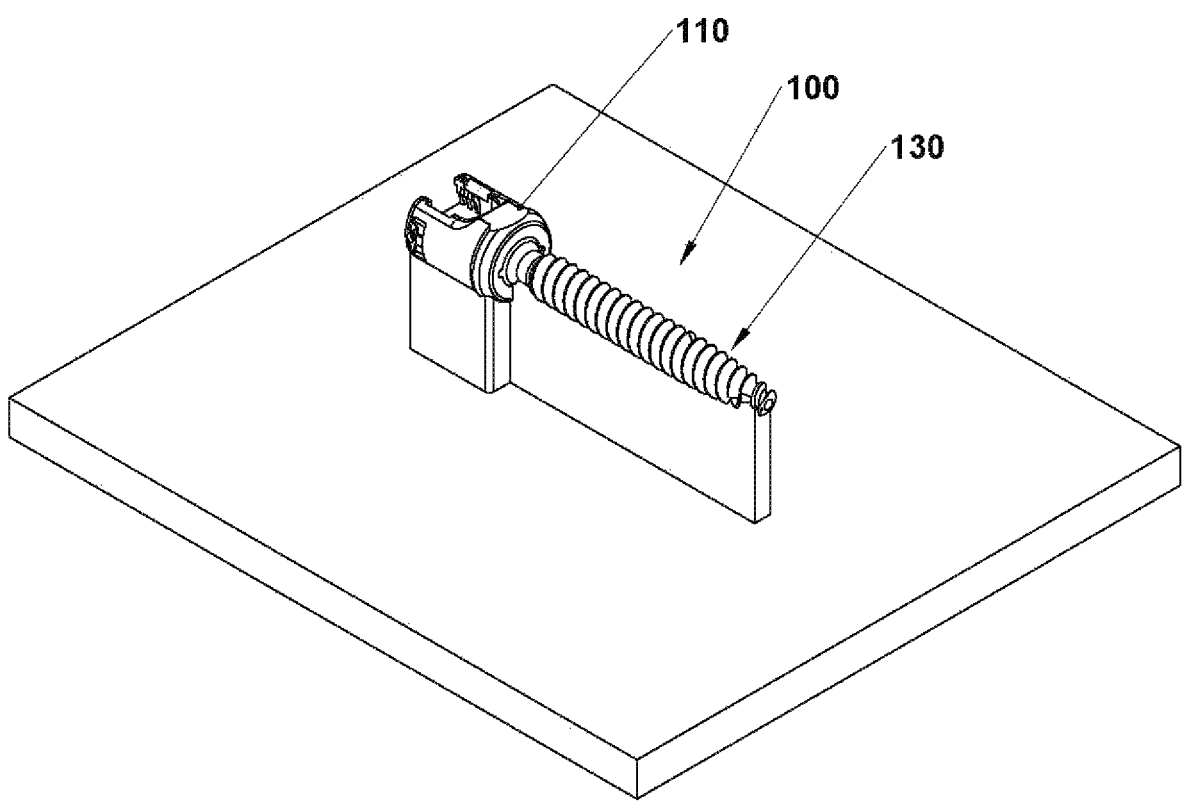
FIG. 3 is a perspective view of a completed surgical implant manufactured using the method according to FIGS. 2A and 2B.

Various embodiments will now be described in detail with reference to the drawings, wherein like reference numerals identify similar or identical elements. As commonly known, the term "proximal" refers to the portion of structure that is closer to the user and the term "distal" refers to the portion of structure that is farther from the user. Further still, directional terms such as front, rear, upper, lower, top, bottom, and the like are used simply for convenience of description and are not intended to limit the disclosure attached hereto.

In the following description, well-known functions or constructions are not described in detail to avoid obscuring the present disclosure in unnecessary detail.

In general, the present disclosure relates to completely assembled surgical implants designed to be manufactured via methods of additive manufacturing, i.e., layer-by-layer techniques. The surgical implants are composed of a number of components configured to move in relation to one another and include a number of features created via additive manufacturing.

With reference to FIG. 1, generally an orthopedic implant is illustrated, for example a polyaxial pedicle screw assembly 100. In general, screw assembly 100 includes a housing 110, an anvil 120, and a bone screw member 130. Bone screw member 130 includes a head 132 and a threaded shaft 134. Aperture 112 has a complimentary shape to both anvil 120 and head 132 of bone screw member 130. Aperture 112 is also configured to allow pivoting and rotation of head 132 of bone screw member 130 while head 132 is positioned there within. The head 132 defines an outer diameter larger than a diameter of aperture 112 and the threaded shaft 134 defines an outer diameter smaller than the diameter of aperture 112, thus preventing head 132 to pass therethrough while permitting the threaded shaft 134 to pass therethrough. Additionally, a proximal end of housing 110 has a U-shaped channel 114 configured to receive an implant, such as a set screw 140 and a spinal rod 150. U-shaped channel 114 defines a threaded section configured for engaging with set screw 140. The head 132 defines an outer dimension such as a diameter that is larger than the U-shaped channel opening, such that the head is unable to pass through the U-shaped channel. Thus, as made in accordance with the present disclosure, a feature of the first unitary, monolithic part is configured and dimensioned to nest and be housed within a cavity of the second unitary, monolithic part such that the two parts are movable relative to one another but are not separable from one another. This approach advantageously eliminates the need for design features required to mechanically assemble parts and then retain the parts in assembled condition. Anvil 120 also may be made during the manufacturing process to be positioned within housing 110 adjacent head 132 of bone screw member 130. Set screw 140 is positionable within housing 110 via threading engagement. Each of housing 110, anvil 120, and head 132 of bone screw member 130 define a cleaning slot 116, 122, and 136, respectively. In some embodiments, screw assembly 100 is fully assembled when anvil 120 and head 132 of bone screw member 130 is positioned within housing 110.

For additional descriptions of polyaxial pedicle screw assemblies, reference can be made to U.S. Pat. Nos. 5,466,237, 5,474,555, 7,087,057, and 9,393,049, the entire content of each is incorporated by reference herein. It is also contemplated that the relationship between the bone screw and housing may be monoaxial, shown and described in U.S. Pat. No. 8,287,576, the entire content of which is incorporated by reference herein, or may be such as to define restricted or preferential angular motion, such as shown and described in U.S. Published Patent Application No. 2015/0272628 U.S. Pat. Nos. 6,736,820, and 8,870,930, the entire content of each is incorporated by reference herein.

Having described the components of screw assembly 100 depicted in FIGS. 1 and 1A, the following description of FIGS. 2A and 2B provides one example of a method of manufacturing (i.e., fabricating) screw assembly 100. Although the method illustrated and described herein as being in a particular order and having particular steps, the method may include some or all of the steps and may be implemented in any order not specifically described. Further, the method illustrated and described herein as being performed by a fabricator, such as ProX DMP 320 by 3D Systems, however, any appropriate fabricator and/or machine may perform the method.

With reference to FIGS. 2A and 2B, steps of a method of additive manufacturing for manufacturing a completely assembled screw assembly 100 are illustrated. In one non-limiting embodiment, the method is noted/identified as method 10, which begins at step 1 by selecting an appropriate additive manufacturing technique, such as Shape Deposition Manufacturing ("SDM"), Selective Laser Power Processing ("SLPP"), Direct Metal Laser Sintering ("DMLS"), Selective Laser Sintering ("SLS"), Selective Laser Melting ("SLM"), Selecting Heating Sintering ("SHS"), Electron Beam Melting ("EBM"), material jetting, binder jetting, or the like. In method 10, screw assembly 100 may be manufactured using SLPP. SLPP utilizes powdered metal and a laser which sinters, cures, or fuses the metal in a selective fashion according to the design intent in thin layers. For a detailed description of exemplary manufacturing methods, reference can be made to U.S. Pat. No. 8,590,157, the entire content of which is hereby incorporated by reference herein.

In step 2, a user will create a three-dimensional model of screw assembly 100. The three-dimensional model depicts all components of screw assembly 100 engaged and/or positioned within one another, i.e. fully assembled. Additionally, the three-dimensional model depicts all the requisite spacing between each component, such that there is relative movement between each component upon the completion of method 10. The three-dimensional model should be created in a format that is compatible with the selected additive manufacturing technique. For example, the three-dimensional model may be created by using CAD software or CAM software on a computer device.

In step 3, the three-dimensional model is converted to a format compatible with a fabricator. The compatible format may be an STL file, an Object file (OBJ file), a Virtual Reality Modeling Language (VRML file), an Additive Manufacturing File (AMF format), G-Code, a Polygon File (PLY format), a 3MF file, or any other appropriate format. In method 10, the selected converted format of the three-dimensional model will be STL file. The STL file format uses a series of linked triangles to recreate the surface geometry of screw assembly 100. The resolution of the STL file should be optimized prior to exporting the STL file to the fabricator. The number of linked triangles directly correlates with the resolution of the STL file, such that as the number of linked triangles increases, the resolution of the STL file increases. After the conversion of the three-dimensional model of screw assembly 100, the user will export the STL file of screw assembly 100 to the fabricator in step 3.

In step 4, the user will prepare the fabricator for manufacturing the completely assembled screw assembly 100. The positioning and the orientation of the screw assembly 100, in relation to a building platform of the fabricator, may be arranged in real-time. The user may also reassess the STL file after establishing the positioning and orientation of screw assembly 100. Additionally, the fabricator is capable of manufacturing more than one screw assembly 100 at a time and may arrange a multitude of screw assemblies 100 in relation to the building platform. The material for screw assembly 100 should be selected while preparing the fabricator. The material can be selected from a group consisting of stainless steel, titanium, cobalt chrome, titanium alloys, polyethylene, polycarbonate, PEEK, polypropylene, and polysulfone or any other appropriate material. The fabricator should be loaded with a sufficient amount of the selected material to manufacture screw assembly 100.

In step 5, user may incorporate support structures within the STL file to provide adequate support for screw assembly 100 during manufacturing. If support structures are needed for adequate manufacturing, user may tilt, fragmentize, and/or manipulate the support structures to minimize the material used for the support structure while providing adequate support for screw assembly 100. Support structures will be removed and discarded upon the completion of screw assembly 100.

In step 6, the fabricator begins to form screw assembly 100. Screw assembly 100 is built layer by layer. A first quantity of material is deposited upon the building platform. Following the STL file of screw assembly 100, a laser will then move across the building platform fusing a portion of the first quantity of material to form a first layer of screw assembly 100.

In step 7, a second quantity of material is deposited upon the building platform overlaying the first layer of screw assembly 100. Again, following the STL file of screw assembly 100, the laser will move across the building platform fusing a portion of the second quantity of material to form a second layer of screw assembly 100.

In step 8, a quantity of material is repeatedly deposited upon the building platform and fused to form additional layers of screw assembly 100 until all components of screw assembly 100 are formed. As indicated above, screw assembly 100 includes housing 110, anvil 120, and bone screw member 130. Each of these components is manufactured simultaneously; however, each of these components may not include the same number of layers of material. Additionally, each component is movable in relation to each other. Further, each component is monolithically formed. Throughout step 16, localized heat treatment can be performed by the fabricator. By applying heat to a specific area of screw assembly 100, the stiffness, elasticity, hardness, tensile strength, yield strength, and other material properties of that specific area can vary from the rest of screw assembly 100, and thus allowing a specialized screw assembly 100 to be manufactured.

Upon completion of step 8, screw assembly 100 is fully assembled with all components freely movable (e.g., pivotable and rotatable) in relation to each other in a polyaxial, rotatable, monoaxial, and/or uniaxial motion. FIG. 3 illustrates a completed screw assembly 100 fully assembled and still supported by the building platform. Method 1 may produce a screw assembly 100 with a surface roughness that promotes bone ingrowth. Preferably, the surface roughness can range from about 75 to about 200 microinches. Also, method 10 allows the user to select the tolerance between each component. The tolerance between each component may range from about 0.007" to about 0.015". By manufacturing screw assembly 100 fully assembled, the cost and time of manufacturing become more efficient.

In step 9, any powder and/or excess material is removed from the completed screw assembly 100 and building platform. Screw assembly 100 is then removed from the building platform. Any support structures used during the manufacturing of screw assembly 100 are also removed from completed screw assembly 100. The fabricator may then conduct a post procedure, such as cleaning screw assembly 100, acid washing screw assembly 100, or any other appropriate post procedure. Other post procedures may be conducted by the user or a secondary machine. Upon completion of method 10, screw assembly 100 is ready for packaging and shipment.

Significantly, each of the screw implant housings and bone screw members is monolithically formed during the layer-by-layer manufacturing process such that the two parts are completed and fully assembled upon completion of the layer-by-layer manufacturing process, without the need for subsequent assembly steps. Not only does this reduce manufacturing steps, but also permits the manufacture of designs that could not be assembled using traditional machining and assembly methods.

With reference to FIGS. 4-6A, alternative embodiments of a screw assembly are illustrated. Each embodiment includes an additional feature formed via method 10 and/or any other appropriate method of additive manufacturing.

Figure 4:
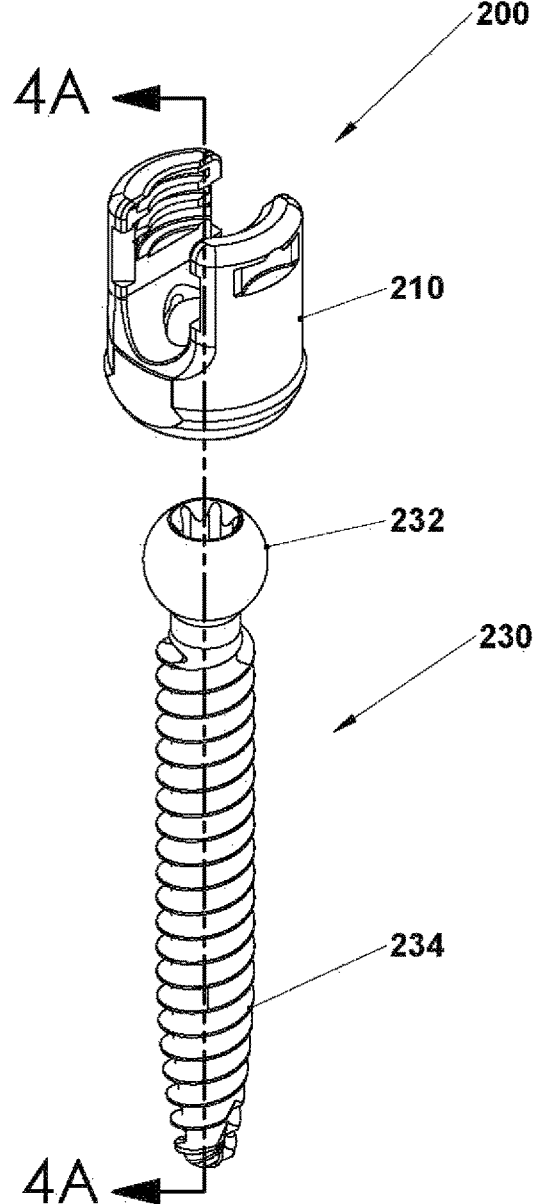
FIG. 4 is an isometric view, with parts separated, of a two piece surgical implant according to an embodiment of the present disclosure.
Figure 4A:
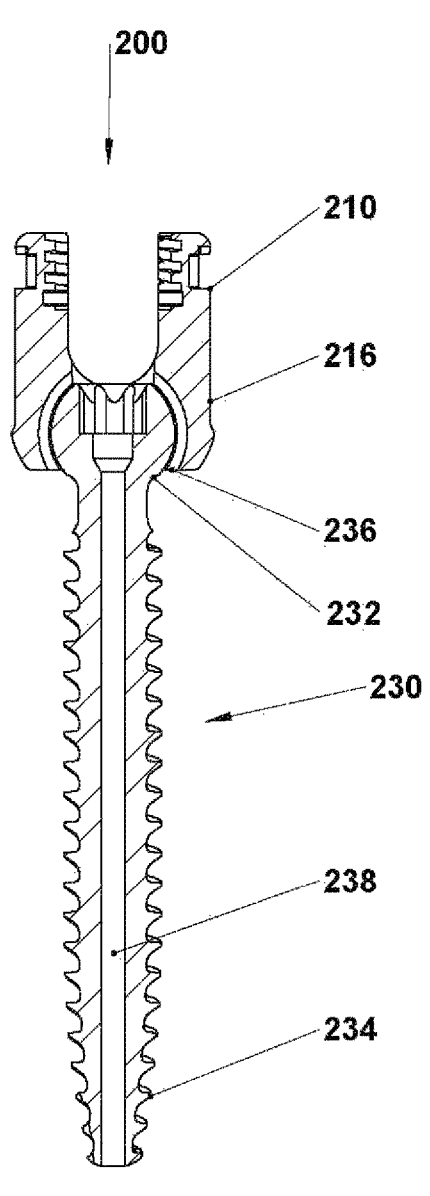
FIG. 4A is a cross-section of the two piece surgical implant of FIG. 4 as taken along section 4A-4A shown in FIG. 4.

Similar to screw assembly 100, a screw assembly 200 includes a housing 210 and a bone screw member 230. Bone screw member 230 includes a head 232 and a threaded shaft 234. In one embodiment, housing 210 of screw assembly 200 and head 232 of bone screw member 230 each define a cleaning slot 216, 236, respectively (FIG. 4A). Cleaning slots 216, 236, along with cleaning slots 116, 122, and 136 of screw assembly 100 (FIG. 1A), allow support material to escape during the post procedure, for example the support material may escape when the fabricator is performing a cleaning procedure. By designing screw assembly 100 and screw assembly 200 to include cleaning slots 116, 122, 136, 216, and 236, respectively, both screw assembly 100 and screw assembly 200 may be manufactured via method 10 as fully assembled. Cleaning slots 216, 236 provide the requisite spacing between housing 210 and head 232 of screw assembly 200, such that housing 210 and head 232 of screw assembly 200 are two individual, independent components of screw assembly 200, which are pivotable and rotatable relative to one another and the other components of screw assembly 200.

Also illustrated in FIG. 4A, some embodiments of screw assembly 200 define a cannula 238. Cannula 238 may extend the entire or partial length of bone screw member 230. Cannula 238 may be defined along a central longitudinal axis of bone screw member 230. Cannula 238 is configured to receive a guide wire or guide pin to assist in the placement of bone screw member 230. For a more detailed description of a screw assembly, reference can be made to U.S. Pat. Nos. 9,393,049 and 8,814,919, the entire content of each is incorporated by reference herein.

Another embodiment of a screw assembly is illustrated in FIGS. 5-5B. Screw assembly 200' includes all of the same components of screw assembly 200, and thus, each component will not be described in detail. In this embodiment, head 232' of bone screw member 230' defines a plurality of apertures and/or impressions/dimples 238'. An inner surface of housing 210' also defines a plurality of apertures and/or impressions/dimples 216'. Both dimples 238' and dimples 216' may be evenly spaced apart or unevenly spaced apart, and in some instances the spacing of dimples 238' will mirror the spacing of dimples 216'. Dimples 238' and 216' may define any appropriate shape, such as a circle, a square, a triangle, and/or an oval. Dimples 238' and 216' are created using method 10. The inclusion of dimples 238' and 216' allow head 232' to mate with the inner surface of housing 210' to allow a polyaxial lock to be created.

Yet another embodiment of a screw assembly is illustrated in FIGS. 6 and 6A. In this embodiment, screw assembly 200" includes all of the same components of screw assembly 200, and thus, each component will not be described in detail. In this embodiment, threaded shaft 234" of bone screw member 230" is designed and made to include a plurality of protrusions 240". The plurality of protrusions 240" is positioned between the thread of bone screw member 230". In one embodiment, the plurality of protrusions 240" do not protrude pass the thread of bone screw member 230". The plurality of protrusions 240" may have any appropriate shape. In some embodiments, screw assembly 200" includes an inner shaft 236" extending through bone screw member 230". Inner shaft 236" may also be designed and made with a plurality of protrusion 242". This design may create a surface of screw assembly 200" promotes bony fixation, ingrowth, and purchase of screw assembly 200". The formation of plurality of protrusions 240" is capable because of method 10. The three-dimensional model of screw assembly 200" will include plurality of protrusion 240", and thus the formation of plurality of protrusion 240" will be completed during the manufacturing of screw assembly 200".

Figures 7, 7A, 7B:
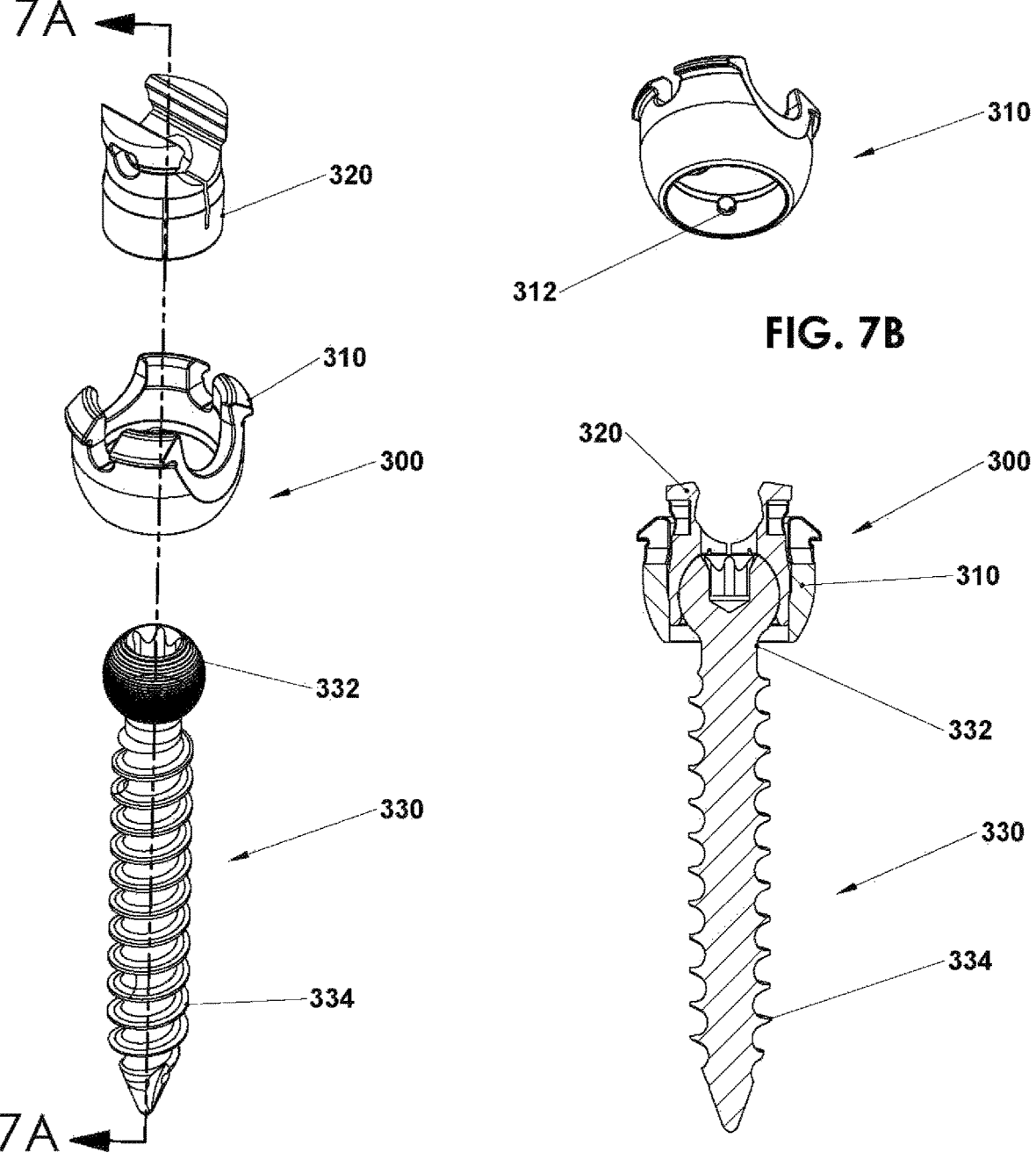
FIG. 7 is an isometric view, with parts separated, of a three piece surgical implant according to an alternate embodiment of the present disclosure.
FIG. 7A is a cross-section of the three piece surgical implant of FIG. 7 as taken along section 7A-7A shown in FIG. 7.
FIG. 7B is a perspective view of a housing of the surgical implant of FIG. 7.

As illustrated in FIGS. 7, 7A, and 7B, a screw assembly 300 is illustrated. Screw assembly 300 is designed to be manufactured via method 10 or any other appropriate method of additive manufacturing. Screw assembly 300 includes a taper lock configuration. Specifically, screw assembly 300 includes an outer housing or coupling 310, an inner housing or collet 320, and a bone screw member 330. A pin 312 is integrally formed within the coupling 310. Bone screw member 330 includes a head 332 and a threaded shaft 334. Bone screw member 330 is configured to be positioned within the coupling 310. Collet 320 is also configured to be positioned within coupling 310. Screw assembly 300 may also be manufactured fully assembled via method 10. Screw assembly 300 is fully assembled when both collet 320 and head 332 of bone screw member 330 are positioned within coupling 310. Method 10 enables screw assembly 300 to be designed with pin 312 integrally formed within the coupling 310. Traditionally methods of manufacturing require pin 312 to be formed separately from coupling 310 and later inserted and/or coupled thereto.

For a more detailed description of a taper lock screw assembly, reference can be made to U.S. Pat. No. 8,814,919, the entire content of which is incorporated by reference herein.

Figures 8, 8A:
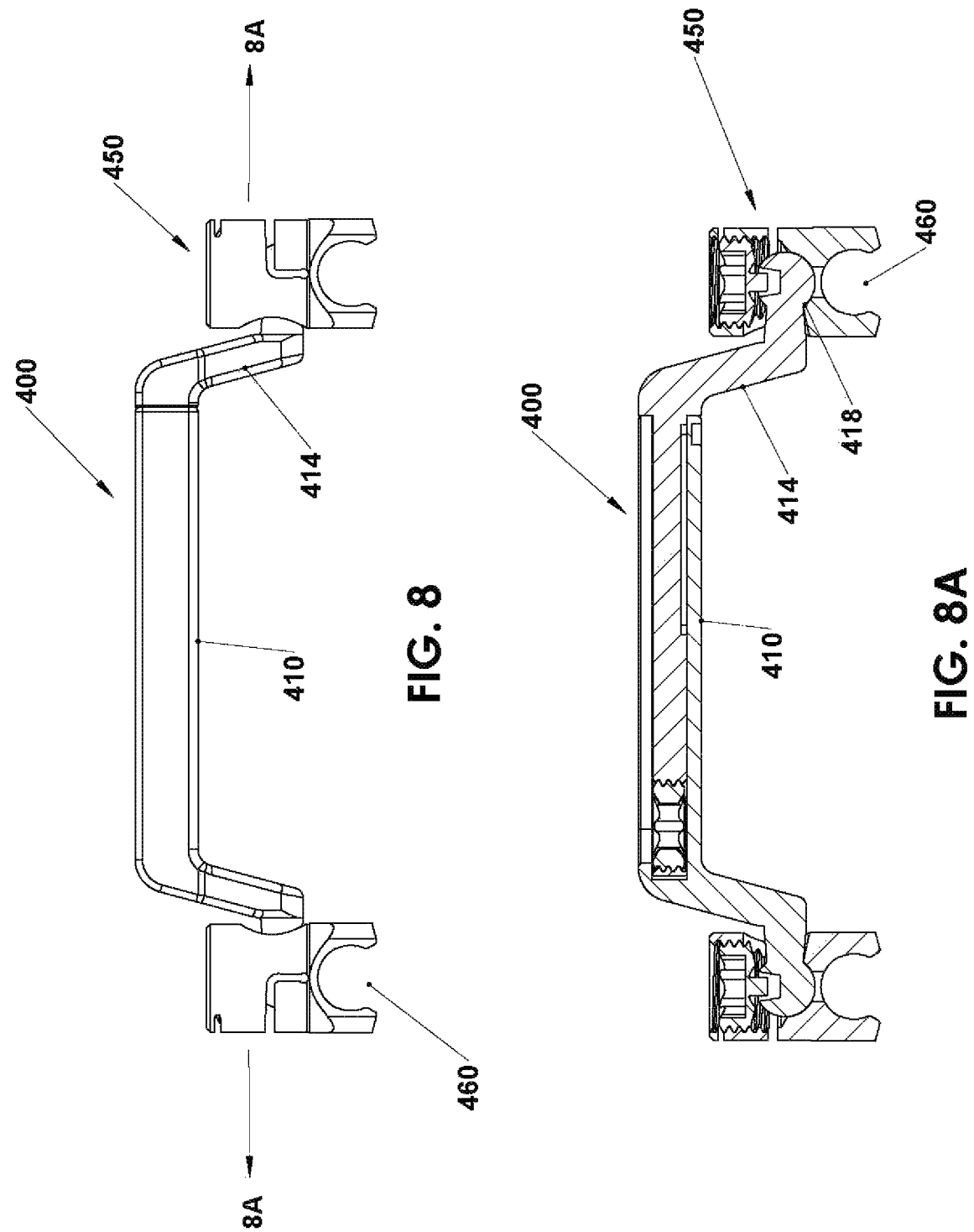
FIG. 8 is a top view of an offset transverse connector according to an embodiment of the present disclosure.
FIG. 8A is a cross-section of the offset transverse connector of FIG. 8 as taken along section 8A-8A shown in FIG. 8.

Method 10 may also be employed to manufacture an offset transverse connector 400, as illustrated in FIGS. 8 and 8A. Transverse connector 400 includes a receiving arm assembly 410 and a spinal rod connector member 450. Receiving arm assembly 410 includes a receiving arm extension 414 having an articulating ball joint 418. Spinal rod connector member 450 defines a spinal rod connecting passage 460. During the manufacturing of transverse connector 400, spinal rod connector member 450 is built around articulating ball joint 418, such that a ball and joint relationship is created between articulating ball joint 418 and spinal rod connector member 450 without including design features to facilitate mechanical assembly of these parts. This method may be used for screw assembly 100, 200, 200', 200", and 300.

For a more detailed description of a transverse connector, reference can be made to International Publication No. WO 2011/006155, the entire content of which is incorporated by reference herein.

Figure 9:
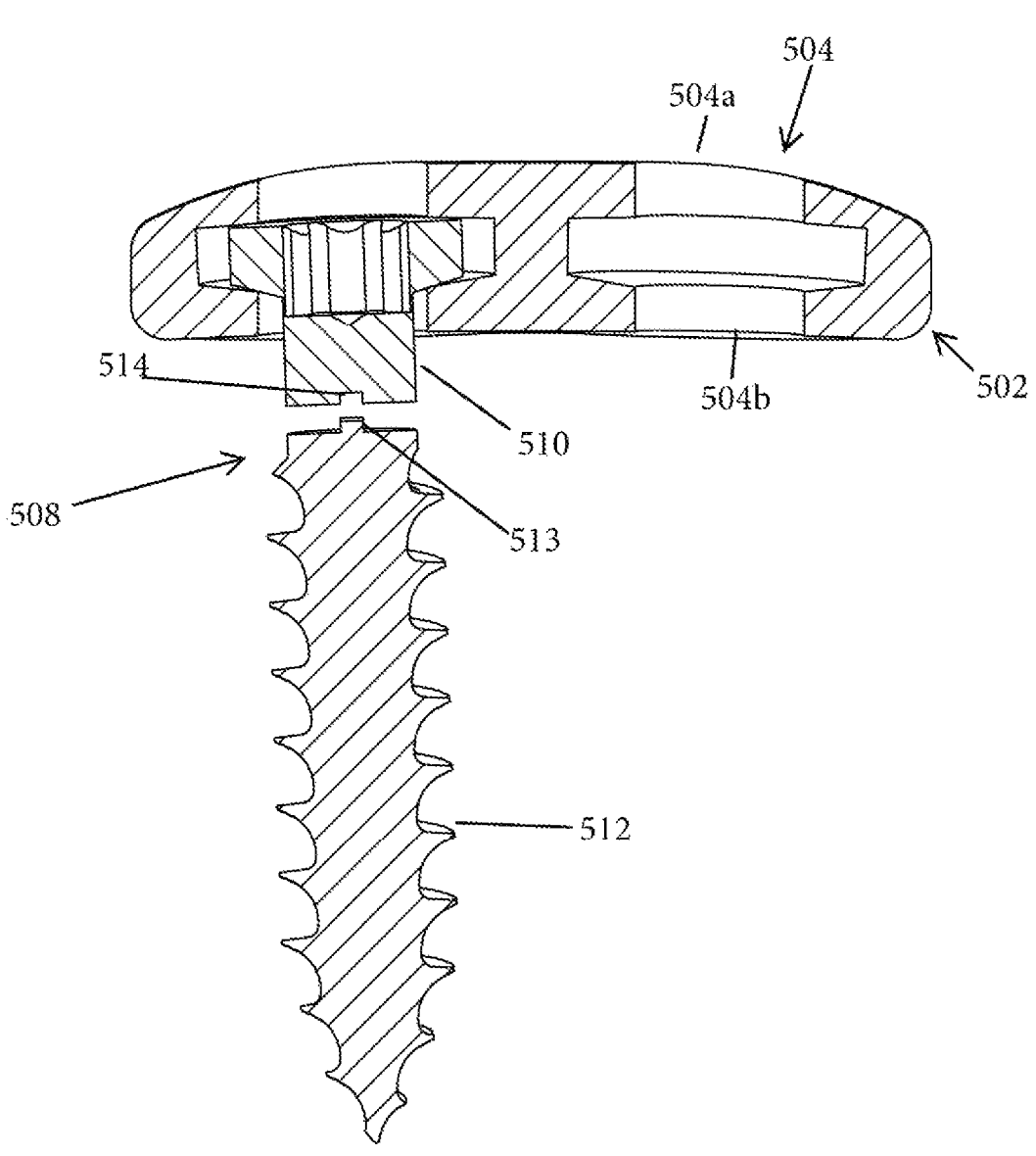
FIG. 9 is a cross-section of a surgical implant according to an embodiment of the present disclosure.
Figure 10:
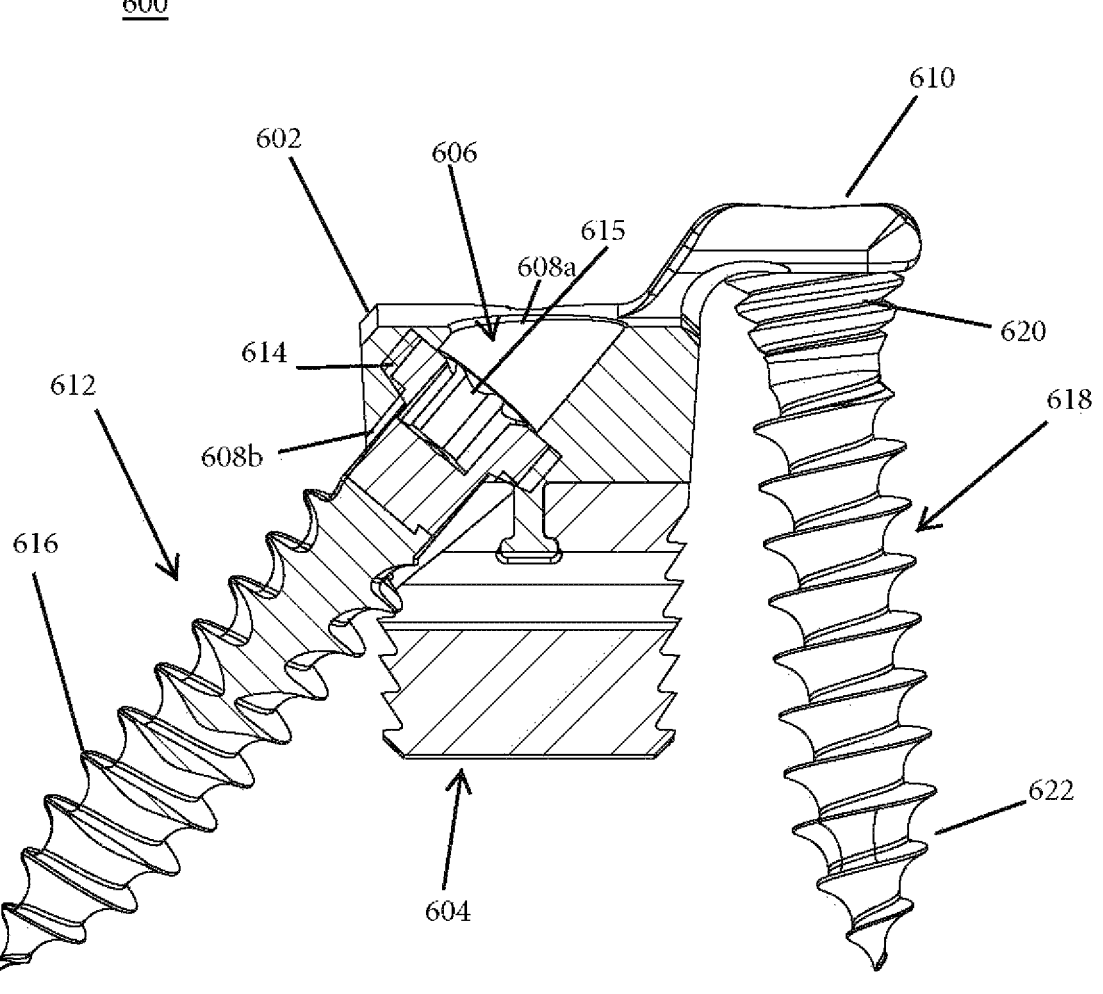
FIG. 10 is a cross-section of a surgical implant according to another embodiment of the present disclosure.
Figure 11:
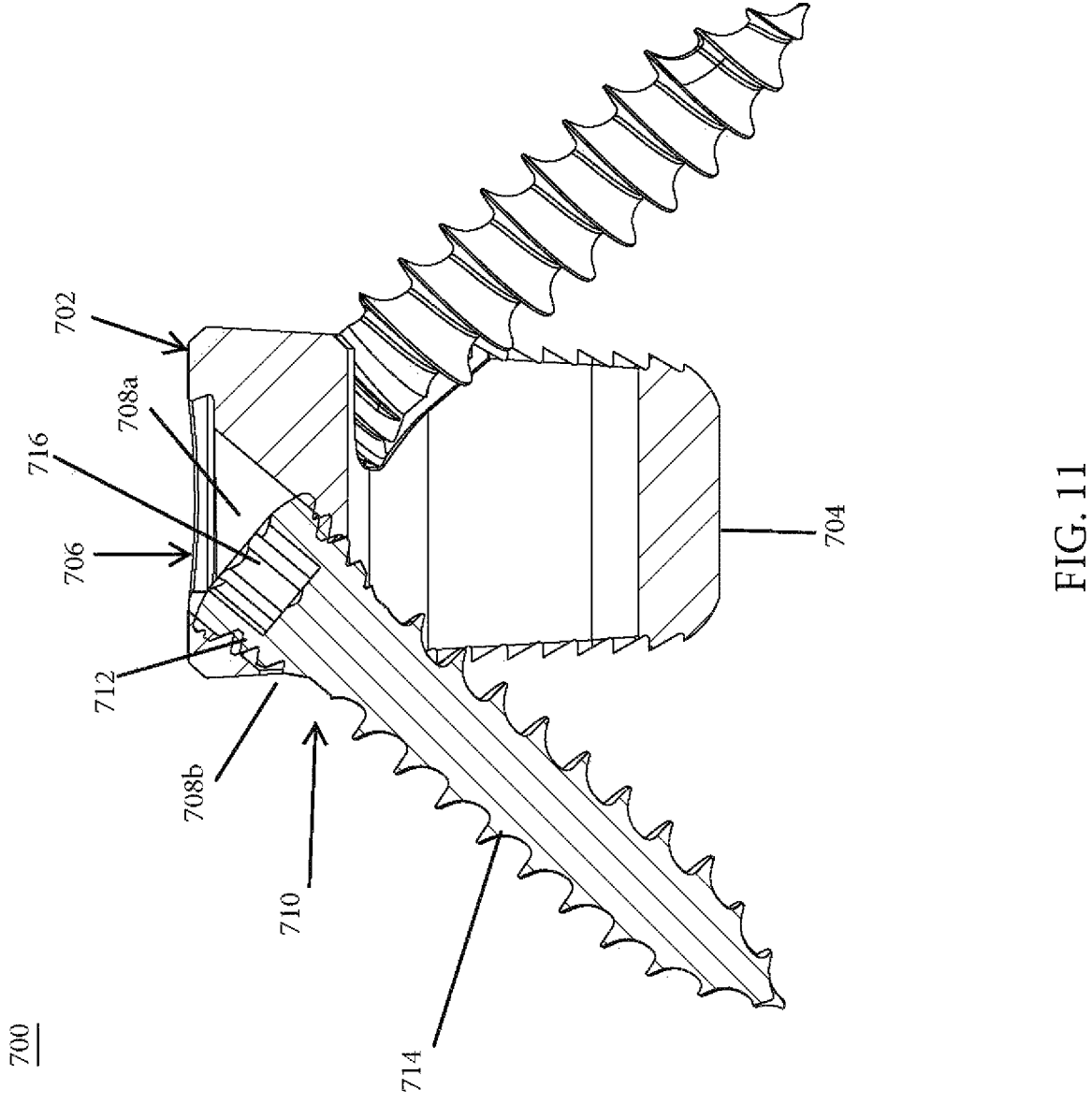
FIG. 11 is a cross-section of a surgical implant according to another embodiment of the present disclosure.

Method 10 may also be employed to manufacture a surgical implant 500, 600, and 700, as illustrated in FIGS. 9-11. Specifically referring to FIG. 9, surgical implant 500 includes a bone plate 502 and a screw assembly 508. The screw assembly 508 includes a head 510 and a threaded shaft 512. The threaded shaft 512 extends from the head 510 and is removably coupled thereto. The threaded shaft 512 and the head 510 may each include a mechanism that facilitates a connection therebetween. In one embodiment, the threaded shaft 512 includes a protrusion 513 extending therefrom and the head 510 defines a groove 514, wherein the groove 514 is configured to receive the protrusion 513 to connect the threaded shaft 512 to the head 510 (FIG. 9). In another embodiment, the thread shaft 512 includes a threaded protrusion configured to screw into a threaded groove defined within the head 510 (not illustrated). The length of threaded shaft 512 is adjustable, in that a user can select a desired length of the threaded shaft 512 prior to assembly. In one embodiment, surgical implant 500 may be included within a surgical kit that provides a plurality of threaded shaft 512 each varying in length and all attachable to the head 510. The bone plate 502 defines a plurality of apertures 504 configured to receive the head 510 of the screw assembly 508. Each aperture of the plurality of apertures 504 defines a cross-section similar to a cross-section of the head 510 of the screw assembly 508. Additionally, each aperture of the plurality of apertures 504 defines a proximal opening 504a and a distal opening 504b, wherein each of the proximal opening 504a and distal opening 504b defines a smaller circumference than a circumference of the head 510 of the screw assembly 508.

A method of implanting surgical implant 500 includes inserting the threaded shaft 512 within a patient and then connecting the threaded shaft 512 with the head 510 of screw assembly 508 and the bone plate 502. A user will select a length of the threaded shaft 512 suitable for the procedure being performed. The thread shaft will be inserted into the patient with a proximal end being accessible after insertion. The user will align the head 510 of the screw assembly 508 with the proximal end of the threaded shaft

512 and connect the two components together by inserting the protrusion 513 of the threaded shaft 512 within the groove 514 of the head 510. The user will align the bone plate 502 as required and then tighten the head 510 to secure the bone plate 502 to the patient.

FIG. 10 generally depicts a surgical implant, such as a two-part spinal implant 600, which is configured to act as an intervertebral implant. The two-part spinal implant 600 is positionable between adjacent vertebrae to take the place of removed spinal disc. The two-part spinal implant 600 generally includes a plate 602, a body 604 and a plurality of first screw assemblies 612 and a plurality of second screw assemblies 618. Each screw assembly of the plurality of first screw assemblies 612 includes a head 614 and a threaded shaft 616 extending therefrom. The head 614 defines an aperture 615 configured to receive a tool, which facilitates the tightening of the first screw 612 assembly within a patient. Each screw assembly of the plurality of second screw assemblies 618 includes a threaded head 620 and a threaded shaft 622 extending therefrom. The body 604 extends from plate 602. Also, the body 604 includes a plurality of apertures 606 and a flange portion 610. Each aperture of the plurality of apertures 606 is configured and dimensioned to receive the head 614 of the first screw assembly 612 and/or the threaded head 620 of the second screw assembly 618. In one embodiment, each aperture of the plurality of apertures 606 defines a cross-section similar to the cross-section of the head 614 of the first screw assembly 612 and/or the threaded head 620 of the second screw assembly 618. Additionally, each aperture of the plurality of apertures 606 defines a proximal opening 608a and a distal opening 608b, wherein each of the proximal opening 608a and distal opening 608b defines a smaller circumference than a circumference of the head 614 of the first screw assembly 612 and/or the threaded head 620 of the second screw assembly 618. In one embodiment, each aperture of the plurality of apertures 606 is defined within the body 604 at angle such that the threaded shaft 616 of the first screw assembly 612 and/or the threaded shaft 622 of the second screw assembly 618 extends from the body 604 at an angle. The flange portion 610 extends from the body 604 and is configured to receive the head 614 of the first screw assembly 612 and/or the threaded head 620 of the second screw assembly 618, thereby connecting the first screw assembly 612 and/or the second screw assembly 618 thereto. The flange portion 610 can extend parallel, perpendicularly, and/or angled from the body 604.

Another embodiment of a two-part spinal implant is illustrated in FIG. 11, and is generally denoted by 700. The two-part spinal implant 700 includes a plate 702, a body 704, and a plurality of screw assemblies 710. Each screw assembly of the plurality of screw assembly 710 includes a threaded head 712 and a threaded shaft 714. Each threaded head 712 defines an aperture 716 configured to receive a tool, which facilitates the tightening of each screw assembly 710. The body 704 extends from the plate 702. The body 704 defines a plurality of apertures 706 configured to receive each threaded head 712 of the plurality of screw assemblies 710. Each aperture of the plurality of apertures 706 defines a cross-section similar to a cross-section of the threaded head 712 of the screw assembly 710. Additionally, each aperture of the plurality of apertures 706 define a proximal opening 708a and a distal opening 708b, wherein each of the proximal opening 708a and distal opening 708b defines a smaller circumference than a circumference of the threaded head 712 of the screw assembly 710. In one embodiment, each aperture of the plurality of apertures 706 is defined within the body 704 at angle such that each threaded shaft 714 of the plurality of screw assemblies 710 extends from the body 704 at an angle.

For a more detailed description of a surgical implant, reference can be made to U.S. Pat. Nos. 9,572,680 and 8,636,738, the entire content of each is incorporated by reference herein.

During manufacturing of the surgical implant 500, the screw assembly 508 and bone plate 502 are manufactured in an assembled condition or state. Using method 10, the bone plate 502 is built simultaneously with the screw assembly 508, such that the finished product of surgical implant 500 results with the head 510 of the screw assembly 508 within an aperture of the plurality of apertures 504 of the bone plate 502. To achieve this effect, the bone plate 502 is built around the head 510 of the screw assembly 508. Also, the proximal end 504*a* and distal end 504*b* of each aperture of the plurality of apertures 504 define a smaller circumference than the head 510 of the screw assembly 508, such that the head 510 of the screw assembly 508 cannot be removed from the bone plate 502. As indicated above, the threaded shaft 512 of the screw assembly 508 can be manufactured at any length. The threaded shaft 512 is manufactured separately from the head 510 and the bone plate 502 and connected to the head 510 after manufacturing is completed. Surgical implants 600 and 700 are manufactured similarly to surgical implant 500. Additionally, the screw assemblies 508, 612, 618, and 710 are all interchangeable and may be used in each disclosed surgical implants 500, 600, and 700. Further, screw assemblies 508, 612, 618, and 710 are interchangeable with screw assembly 100.

Further, method 10 may be used to form any fully assembled surgical implant with multiple components or to make subassemblies. A three-dimensional model of any surgical implant with multiple components will be designed to include a cleaning slot and/or any design feature that provides the requisite spacing between each component, thereby allowing simultaneously production via method 10.

Additionally, method 10 may be used to form a fully assembled joint of any surgical implant. For example, the fully assembled joint may be a ball and socket joint, a pivot joint, a hinge joint, a saddle joint, condyloid joint, a gliding joint, ellipsoid joint, and any other joint commonly used in surgical implants. Method 10 manufactures each component of the joint simultaneously, for example, a ball component of a ball and socket joint will be formed simultaneously with the socket component by having the ball component being built within the socket component. This technique allows fabrication of assembled devices that are too complicated for traditional manufacturing techniques. In one non limiting example, a polyaxial pedicle screw may be manufactured with the spherical head of the screw member already positioned in the spherical cavity in the receiver where the top and bottom openings of the receiver are smaller than the outside diameter of the spherical head thereby retaining the head of the screw in the receiver due to the reduced sizes of the openings in the receiver and eliminating additional structures for retaining the head of the screw in the receiver. This same process is applicable to all types of joints.

One example of a potentially desirable sliding connection may be an adjustable occipital plate. Typically, an occipital plate includes a rod receiving portion slidably mounted through a slot in a plate to permit repositioning of a rod receiving housing relative to the plate. In some embodiments, a nut on one side of the slot is mounted to a shaft extending from the rod-receiving housing through the slot.

In accordance with the present disclosure, it is contemplated that the nut may be replaced with a flange monolithically formed as part of the shaft extending from the rod-receiving housing in a manufacturing process which builds plate, rod-receiving housing, shaft, and flange in a layer-by-layer manufacturing process. Similarly, in some situations, a telescoping relationship of parts may be desired, but with pre-formed stops or guides to control or limit motion, such as in rod to rod connectors as discussed herein or so-called growing rods that permit extension of an implanted rod as youthful patient grows.

For a more detailed description of an adjustable occipital plate, reference can be made to U.S. Pat. No. 8,894,694, the entire content of which is incorporated by reference herein.

Further, method 10 may be used to simultaneously form design features that are usually produced after the completion of a surgical implant via a traditional manufacturing method. For example, method 10 may be used to form any surgical implant including any desired surface texture, such as a dimpled surface, and/or any desired surface roughness to promote bone ingrowth or through growth. This allows for bone growth into the surgical implant or bone growth through the surgical implant.

The method of the present disclosure may be used to fabricate complex functional assemblies which are difficult to design for assembly in such a manner to withstand required static and fatigue testing. For example, expandable interbody implants or expandable vertebral body replacements may be fabricated in whole or in part using the techniques of the present disclosure so that the interrelated moving parts are fully assembled upon manufacture and do not require intricate assembly techniques. Accommodating such designs for assembly may compromise the structural integrity of the design to withstand testing and further complicate the design process. By way of example only, US Patent Application Publication No. 2016/0166396 and U.S. Pat. Nos. 8,882,840 and 9,566,163 disclose examples of expandable interbody implants, and US Patent Application Publication Nos. 2014/0277503 and 2017/0079807 disclose expandable vertebral body replacement devices. All of the foregoing patents and applications are incorporated herein by reference. All or portions of these or similar devices may be fabricated using the techniques disclosed herein in order to obviate the need for complex designs and assembly techniques.

Persons skilled in the art will understand that the structure and methods specifically described herein and shown in the accompanying figures are non-limiting exemplary embodiment, and that the description, disclosure, and figures should be construed merely, as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements features of certain other embodiment without departing from the scope of the present disclosure, and that such modification and variations are also included within the scope of the present disclosure. Accordingly, the subject matter of the present disclosure is not limited by what has been particularly shown and described.

For example, while the foregoing description has largely focused on spinal implants and their manufacture, and more particularly multi-part spinal implants wherein the spinal implants preferably are made of titanium based materials, it is contemplated that the advantages disclosed herein may find application in other situations, such as general orthopedics.

By way of example, it is contemplated that the advantages of simultaneously forming moving components as described herein may provide advantages in the creation of implants for small joints, such as fingers or toes, where the movable mechanism must be fairly small and the formation of separate parts and their assembly using traditional manufacturing techniques limit the implant design which may be accomplished. The techniques described herein may permit the manufacture of small joint designs which previously have not been practical or achievable.

In addition, it is contemplated that the techniques may find application to larger joints, such as a hip or shoulder joints. While metal on metal joints have exhibited drawbacks in load bearing application, it is contemplated that the techniques disclosed herein may be used to form such joint implants from non-metallic materials.

In addition, the techniques disclosed herein may be used to create subassemblies, which may then be combined with separately manufactured components made by different techniques. For example, proven hip implants designs include implants with a metal acetabular cup and a polymeric bearing linear between the cup and the ball head of a femoral stem component. Mechanical designs have been proposed to retain the ball head within the bearing liner. See, for example, U.S. Pat. No. 4,798,610, the entire content of which is incorporated by reference herein. Instead of separately forming the polymeric bearing liner and the locking mechanism to hold the ball head, it is contemplated that the bearing liner component and the ball head and possibly the stem could be formed by layer-by-layer techniques as described herein with the ball head disposed in the bearing liner component without the need for additional retainer mechanisms, e.g., the bearing liner would surround the ball head sufficiently such that no additional retainer mechanism would be necessary. The bearing liner and ball head assembly could then be assembled together with a metal acetabular cup, which is known to perform well juxtaposed to acetabular bone. Alternatively, as layer-by-layer techniques evolve, it may be possible to simultaneously form components from different materials, such as to form the bearing liner component from a polymeric component while simultaneously forming the ball head and stem and/or acetabular cup from metal.

The invention claimed is:

1. A method of manufacturing a housing assembly of a pedicle screw comprising:
   alternately depositing and heating successive layers of a first source material to form a first portion of a first part of the pedicle screw;
   alternately depositing and heating successive layers of a second source material subsequent to the formation of the first portion to form a second part of the pedicle screw, the second part being retained by the first part; and
   alternately depositing and heating successive layers of the first source material subsequent to the formation of the first portion to form a second portion of the first part, wherein the first part and the second part are fully assembled upon completion of the formation of the first part and the second part.

2. The method of claim 1, wherein forming the second part includes forming a support structure such that upon completion of the formation of the first part and the second part, the second part is attached to the first part by the support structure.

3. The method of claim 2, further comprising breaking the support structure such that the second part is movable relative to the first part.

4. The method of claim 1, wherein forming the second part includes forming an anvil shaped to support a spinal rod.

5. The method of claim 1, wherein depositing each of the first and second source materials includes depositing titanium.

6. The method of claim 1, wherein forming the first part and the second part includes forming at least some of the first part and at least some of the second part simultaneously.

7. The method of claim 1, further comprising alternately depositing and heating successive layers of a third source material to form a bone screw of a pedicle screw, a bone screw adapted for securement within the first part.

8. The method of claim 1, wherein forming the first part includes forming a housing.

9. A method of forming a pedicle screw housing assembly in a single continuous process comprising:
   alternately depositing and heating successive layers of a first source material to form a first part of the pedicle screw;
   alternately depositing and heating successive layers of a second source material to form a second part of the pedicle screw,
   wherein the first part and the second part are formed such that the second part is captured within the first part, and
   wherein forming the second part includes forming an anvil sized to fit within an interior cavity of the first part and having a surface with a saddle shape to receive a spinal rod.

10. The method of claim 9, wherein the first part and the second part are formed monolithically and are connected to each other through one or more support structures, the one or more support structures having a stress failure value lower than the first part or the second part.

11. The method of claim 10, further comprising applying force to the second part relative to the first part to break the one or more support structures such that the second part is moveable within the first part.

12. The method of claim 9, further comprising alternately depositing and heating successive layers of a third source material to form a screw, the formed screw being retainable within the first part and being shaped to receive the anvil while retained within the first part.

13. The method of claim 9, wherein depositing each of the first and second source materials includes depositing titanium.

14. A pedicle screw housing assembly formed through an additive manufacturing process comprising:
   a first part formed layer-by-layer by depositing and fusing a first plurality of successive layers of a first material; and
   a second part disposed within a cavity of the first part, the second part formed layer-by-layer by depositing and fusing a second plurality of successive layers of a second material, an initial layer of the second plurality of successive layers being formed prior to the formation of a final layer of the first plurality of successive layers, and a third part disposed within the cavity of the first part, the third part formed layer-by-layer by depositing and fusing a third plurality of successive layers of a third material, wherein the second part is formed monolithically with the first part such that a weakened portion bridges the first part and the second part, the weakened portion being breakable upon application of a torque to one of the first part and the second part relative to the other of the first part and the second part, and wherein the third part is a cannulated bone fastener with a plurality of fenestrations extending from an outer surface of the cannulated bone fastener to an inner surface of the cannulated bone fastener that defines the cannulation.

15. The assembly of claim 14, wherein the second part is shaped to receive a spinal rod disposed within the first part.

16. The assembly of claim 14, wherein the weakened portion includes one or more support structures positioned such that the second part bears onto at least one of the one or more support structures.

17. The assembly of claim 16, wherein a portion of the assembly traversing the respective first part, one or more support structures and second part comprises successive layers of material formed through a continuous process.

18. The assembly of claim 14, wherein the first material of the first part and the second material of the second part are titanium.

19. The assembly of claim 14, wherein the first part is a U-shaped housing and the second part is an insert.

* * * * *